(12) United States Patent
Zhan et al.

(10) Patent No.: US 12,118,896 B2
(45) Date of Patent: Oct. 15, 2024

(54) VISUAL BIONIC DIGESTIVE SYSTEM FOR HUMAN GASTROINTESTINAL TRACT MODEL

(71) Applicant: Jiangnan University, Wuxi (CN)

(72) Inventors: Xiaobei Zhan, Wuxi (CN); Zhitao Li, Wuxi (CN); Minjie Gao, Wuxi (CN); Wenlong Zhang, Wuxi (CN); Zhiyong Zheng, Wuxi (CN); Xingqiao Peng, Wuxi (CN); Yun Jiang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 1807 days.

(21) Appl. No.: 16/121,720

(22) Filed: Sep. 5, 2018

(65) Prior Publication Data
US 2019/0228681 A1 Jul. 25, 2019

Related U.S. Application Data

(63) Continuation of application No. PCT/CN2018/081004, filed on Mar. 29, 2018.

(30) Foreign Application Priority Data

Jan. 24, 2018 (CN) .......................... 201810068728.6
Jan. 24, 2018 (CN) .......................... 201810069219.5
Jan. 24, 2018 (CN) .......................... 201810069220.8

(51) Int. Cl.
*G09B 23/32* (2006.01)
*B01L 3/00* (2006.01)
(Continued)

(52) U.S. Cl.
CPC ............ *G09B 23/32* (2013.01); *B01L 3/5085* (2013.01); *B01L 3/561* (2013.01); *B01L 3/567* (2013.01);
(Continued)

(58) Field of Classification Search
CPC ..... G09B 23/32; G09B 23/303; B01L 3/5085; B01L 3/561; B01L 3/567; B01L 2200/06;
(Continued)

(56) References Cited

U.S. PATENT DOCUMENTS

2010/0256667 A1    10/2010  Ashby et al.
2011/0020780 A1*    1/2011  Alric ...................... G09B 23/32
                                                                434/272

FOREIGN PATENT DOCUMENTS

CN    103675205 A    3/2014
CN    103740589 A    4/2014
(Continued)

*Primary Examiner* — Xiaoyun R Xu
(74) *Attorney, Agent, or Firm* — IPRO, PLLC (57) ABSTRACT

The present invention discloses a visual bionic digestive system for a human gastrointestinal tract model, and belongs to the field of bionic digestive systems. The visual bionic digestive system for a human gastrointestinal tract model comprises a reaction system and a control system; the reaction system comprises a bionic stomach system, a bionic small intestine system, a bionic large intestine system and a filtering system; the control system comprises a PLC, peristaltic pumps, and a circulating water tank; the water inlet pipes of the bionic stomach system, the bionic small intestine system, and the bionic large intestine system are connected to a water outlet of the circulating water tank through water pipes; the water outlet pipes of the bionic stomach system, the bionic small intestine system, and the bionic large intestine system are connected to a water inlet of the circulating water tank through water pipes, solenoid valves are arranged on the water pipes, and the solenoid valves on the water pipes are controlled by the PLC. The bionic digestive system provided by the present invention has the advantages of strong visibility, high automation, device modularization, and simple and effective gastrointestinal peristalsis simulation way.

10 Claims, 5 Drawing Sheets

(51) Int. Cl.
*G09B 23/30* (2006.01)
*G01N 33/02* (2006.01)
(52) U.S. Cl.
CPC ........ *G09B 23/303* (2013.01); *B01L 2200/06* (2013.01); *B01L 2300/049* (2013.01); *B01L 2300/08* (2013.01); *B01L 2300/0832* (2013.01); *B01L 2300/0874* (2013.01); *B01L 2400/0666* (2013.01); *G01N 33/02* (2013.01)
(58) Field of Classification Search
CPC ........... B01L 2300/049; B01L 2300/08; B01L 2300/0832; B01L 2300/0874; B01L 2400/0666; G01N 33/02
See application file for complete search history.

(56) References Cited

FOREIGN PATENT DOCUMENTS

| | | |
|---|---|---|
| CN | 105702146 A | 6/2016 |
| CN | 105842407 A | 8/2016 |

* cited by examiner

VISUAL BIONIC DIGESTIVE SYSTEM FOR HUMAN GASTROINTESTINAL TRACT MODEL

TECHNICAL FIELD

The present invention relates to a visual bionic digestive system for a human gastrointestinal tract model, and belongs to the field of bionic digestive systems.

BACKGROUND

The in vitro simulation device for the human digestive tract has been continuously popularized to provide a tremendous convenience for food science and human nutrition researches, and has gradually been accepted by the academic community. In the research process of modern food processing, the objective and accurate assessment of the digestive process of food in the human body is crucial for determining the role of food components. The use of the in vitro simulation device for the human digestive tract plays a key role in assessing the digestive process of food in the human body. The research and development of a novel in vitro simulation device for the human digestive tract has provided a great convenience for the study of human intestinal microorganisms. By simulating the digestive processes of different samples in an in vitro model and the effect on the intestinal microorganisms, it will provide vast amounts of valuable data for the research and development of novel functional foods, which is incomparable to mouse experiments or human volunteer experiments.

A triangular flask or beaker is generally used as a simulated gastric digestion device in the prior art. In a simulated digestion experiment, a certain amount of food is first put into the triangular flask or beaker, then the simulated gastric or intestinal juice is added to the triangular flask, and then the triangular flask or beaker is placed on a thermostatic water bath shaker to be digested by vibration for a period of time. The process is a process for simulating the digestion of the human intestinal tract. After the digestion is completed, the digested and undigested substances are separated by centrifugation or filtering. When the triangular flask or beaker is used as a simulated gastrointestinal digestion device, the digestive products in the triangular flask or beaker have an inhibitory effect on the digestion reaction, resulting in an inaccurate measurement result for such digestion experiments.

Compared with the triangular flask or beaker as a simulated human intestinal digestion device, Molly et al. in Belgium developed a multi-chamber dynamic digestive tract simulation device in 1993. In the early stages of research and development, the model comprises only five computer-controlled reactors connected in series to simulate the human duodenum/jejunum, ileum, cecum/ascending colon, transverse colon, and descending colon respectively. Subsequently, in 2001, De Boever et al. added a simulated stomach reactor in front of a duodenal/jejunal reactor, making it a complete in vitro digestive tract model.

CN104851346A discloses a modular in vitro simulation system for the animal digestive tract and a human intestinal tract simulation method of the modular in vitro simulation system. The modular in vitro simulation system for the animal digestive tract comprises five parts of stomach, small intestine, ascending colon, transverse colon and descending colon. The core of each part is a reaction tank, and the reaction tank is used for storing a digestive juice and an enterobacterial medium and is a place for simulating food digestion and growth of enterobacteria. The water interlayer of each reaction tank is communicated with a thermostatic water bath to achieve a 37° C. constant temperature effect. The peristalsis of each reaction tank is simulated by magnetic stirring. CN102399692A discloses a full-automatic in vitro simulated model device for intestinal floras, comprising an airway system, a fermentation system and a control system; the fermentation system comprises a culture medium bottle with a stirring device and a bioreactor; the control system comprises a display screen, a central processor, a pH controller, a temperature control system, a peristaltic pump, etc.

The above two kinds of simulated human and animal gastrointestinal digestion devices use stirring as a means of simulating the gastrointestinal peristalsis. The drawback is that the motion of the food produced by stirring in the gastrointestinal tract differs greatly from the actual situation, so the real gastrointestinal tract cannot be well simulated; one of the simulated digestion devices uses only one reactor to simulate the gastrointestinal tract, and its drawback is that the intermediates and products produced by the reaction are accumulated in the reactor to inhibit digestive enzymes.

SUMMARY

The present invention aims at the limitation of the existing in vitro simulated human gastrointestinal digestion device to provide a visual bionic digestive system for a human intestinal tract model, which has strong visibility, high automation, device modularization, and a simple and effective gastrointestinal peristalsis simulation way.

The first objective of the present invention is to provide a visual bionic digestive system for a human gastrointestinal tract model. The visual bionic digestive system for a human gastrointestinal tract model comprises a reaction system and a control system, wherein the reaction system comprises a bionic stomach system, a bionic small intestine system, a bionic large intestine system and a filtering system; the control system comprises a PLC (Programmable Logic Controller), peristaltic pumps, and a circulating water tank; the water inlet pipes of the bionic stomach system, the bionic small intestine system, and the bionic large intestine system are connected to a water outlet of the circulating water tank through water pipes; the water outlet pipes of the bionic stomach system, the bionic small intestine system, and the bionic large intestine system are connected to a water inlet of the circulating water tank through water pipes, solenoid valves are arranged on the water pipes, and the solenoid valves on the water pipes are controlled by the PLC.

In one embodiment, the visual bionic digestive system for a human intestinal model further comprises a sample delivery device, the sample delivery device comprises a first gas bottle and a plurality of sample bottles, the plurality of sample bottles is connected to the bionic stomach system through the peristaltic pump, one opening of the first gas bottle is communicated with one of the plurality of sample bottles, and the other opening is connected to the bionic stomach system through a solenoid valve.

In one embodiment, the bionic stomach system is formed by sequentially connecting a first adapter, a first cylindrical reactor, a spherical reactor, a first sampler, a second cylindrical reactor, and a second adapter through flanges, a sample is input from the first adapter and is output from the second adapter, and the second adapter is connected to the bionic small intestine system through the peristaltic pump.

In one embodiment, the bionic small intestine system is formed by sequentially connecting a third adapter, a third cylindrical reactor, a second sampler, a fourth cylindrical reactor, and a fourth adapter through flanges; the second sampling bottle is provided with a lower end opening and a syringe pump, the third adapter is connected to a digestive juice bottle through the peristaltic pump, and the digestive juice bottle is communicated with a second gas bottle.

In one embodiment, the bionic large intestine system is formed by sequentially connecting a fifth adapter, a fifth cylindrical reactor, a third sampler, a sixth cylindrical reactor, and a sixth adapter through flanges; the fifth adapter is connected to the lower end opening of the second sampling bottle through the peristaltic pump, and the third sampling bottle is provided with a lower end opening.

In one embodiment, the visual bionic digestive system for a human intestinal model further comprises a filtering device connected to the fourth adapter of the bionic small intestine system.

In one embodiment, the first sampling bottle of the bionic stomach system, the second sampling bottle of the bionic small intestine system and the third sampling bottle of the bionic large intestine system are all provided with two glass tubes, into which pH electrode probes and microscope probes are respectively inserted.

In one embodiment, the PLC controls the start-stop and on-off of the peristaltic pumps, the syringe pumps, and the solenoid valves through leads.

In one embodiment, the first gas bottle and the second gas bottle are filled with a mixed gas of $N_2$ and $CO_2$.

In one embodiment, the third sampling bottle is provided with an inoculation port for inoculating the large intestine system with intestinal microorganisms.

The second objective of the present invention is to provide a visual bionic gastric body digestion reactor, which comprises a first adapter, a second adapter, a reactor, a latex bionic stomach, a first sampler, and a thermostatic circulating water tank, wherein the reactor comprises a first cylindrical reactor, a spherical reactor and a second cylindrical reactor, and the reactors are all provided with an output pipe and an input pipe, which are connected with the thermostatic circulating water tank through silicon tubes, and the first adapter, the first cylindrical reactor, the spherical reactor, the first sampler, the second cylindrical reactor, and the second adapter are sequentially connected through flanges; the latex bionic stomach comprises a latex bionic gastric body, a latex bionic gastric antrum, and a latex bionic pylorus, which are respectively placed in the first cylindrical reactor, the spherical reactor, and the second cylindrical reactor.

In one embodiment, both the first adapter and the second adapter are hollow hemispheres, flanges are provided at the openings of the hollow hemispheres, the arc top of the first adapter is provided with an input pipe, and the arc top of the second adapter is provided with an output pipe.

In one embodiment, the spherical reactor is a hollow sphere, and two mutually vertical openings are formed in the hollow sphere, the two openings divide the great circle of the hollow sphere into a major arc and a minor arc, and an input pipe and an output pipe of a spherical reaction bottle are arranged on the major arc; both ends of the latex bionic gastric antrum are respectively communicated with a section of latex tube, and the ports of the two sections of latex tubes are respectively extended from the two openings of the hollow sphere to be turned inside out, and the end parts of the latex tubes turned inside out to be exposed to the outside of the flanges are sleeved on the flanges.

In one embodiment, the first sampler is a hollow tube body, the left end and right end openings of the hollow tube body are respectively provided with a flange, and the side body of the hollow tube body is provided with three glass tubes which are vertically communicated with the hollow tube body; two of the three glass tubes are vertically arranged and provided with upward openings, and the ports of the glass tubes are provided with external threads; another glass tube is horizontally arranged, the port of the glass tube is provided with a ground opening, and the ground opening is plugged with a rubber plug.

In one embodiment, after the first adapter, the first cylindrical reactor, the spherical reactor, the first sampler, the first cylindrical reactor, and the second adapter are sequentially connected through flanges, the two flanges connected are clamped with a clamp.

In one embodiment, three silicone tubes communicated with the input pipes of the first cylindrical reactor, the spherical reactor, and the second cylindrical reactor join to form a total input silicone tube, which is communicated with a water outlet of the thermostatic circulating water tank, the three input silicone tubes are respectively provided with a valve, and a gear pump is arranged on the total input silicone tube.

In one embodiment, the first cylindrical reactor is vertically placed, and the second cylindrical reactor is horizontally placed.

In one embodiment, the components of the visual bionic gastric body digestion reactor are made of glass.

The third objective of the present invention is to provide a visual in vitro bionic intestinal body digestion reactor, which comprises a third cylindrical reactor, a fourth cylindrical reactor, a second sampler, and a thermostatic circulating water tank, wherein the third cylindrical reactor, the fourth cylindrical reactor and the second sampler are sequentially butt jointed through flanges; the output pipes of the third cylindrical reactor and the fourth cylindrical reactor are respectively connected with branch output silicone tubes, which join to form a total output silicone tube connected to a water return port of the thermostatic circulating water tank, the input pipes of the third cylindrical reactor and the fourth cylindrical reactor are respectively connected with branch input silicone tubes, which join to form a total input silicone tube connected to the water outlet of the thermostatic circulating water tank, valves are arranged on each branch output silicone tube and each branch input silicone tube, and gear pumps are arranged on the total output silicone tube and the total input silicone tube.

In one embodiment, the visual in vitro bionic intestinal digestion reactor further comprises a third adapter which is butt jointed with the third cylindrical reactor, a fourth adapter which is butt jointed with the fourth cylindrical reactor, and bionic intestinal tracts which are respectively placed in the third cylindrical reactor and the fourth cylindrical reactor.

In one embodiment, both the third adapter and the fourth adapter are hollow hemispheres, flanges are arranged at the openings of the hollow hemispheres, and the arc top of the third adapter is provided with an input pipe, and the arc top of the fourth adapter is provided with an output pipe. In one embodiment, the third cylindrical reactor and the fourth cylindrical reactor are hollow tube bodies, the left end and right end openings are respectively provided with a flange, both ends of the bionic intestinal tract are respectively extended from the two openings of the hollow tube body to be turned inside out, and the end parts of the latex tubes turned inside out to be exposed to the outside of the flanges are sleeved on the flanges.

In one embodiment, the second sampler is a hollow tube body, the left end and right end openings of the hollow tube body are respectively provided with a flange, and the side of the hollow tube body is provided with five glass tubes which are vertically communicated with the hollow tube body; two of the five glass tubes are provided with vertically upward openings, and the ports of the two glass tubes are provided with external threads; another two glass tubes are provided with vertically downward openings, the port of one glass tube is provided with external threads, and the outer wall of the port of the other glass tube is provided with left-handed threads; one glass tube is horizontally arranged, the port thereof is provided with a ground opening, and the ground opening is plugged with a rubber plug.

In one embodiment, after the third adapter, the third cylindrical reactor, the second sampler, the fourth cylindrical reactor, and the fourth adapter are sequentially connected through flanges, the two flanges connected are clamped with a clamp.

In one embodiment, reaction bottles and latex bionic intestinal tracts of different sizes are used to simulate the small intestine and the large intestine respectively.

In one embodiment, the third cylindrical reactor, the fourth cylindrical reactor, the third adapter, the fourth adapter and the second sampler are made of glass.

The fourth objective of the present invention is to provide application of any one visual bionic digestive system for a human gastrointestinal tract model in the fields of food, medicine and feed.

The fifth objective of the present invention is to provide application of any one visual bionic gastric body digestion reactor in the fields of food, medicine and feed.

The sixth objective of the present invention is to provide application of any one visual in vitro bionic intestinal digestion reactor in the fields of food, medicine and feed.

The beneficial effects of the present invention are as follows:

The visual bionic digestive system for a human intestinal tract model provided by the present invention has the following advantages.

Compared with the existing simulated gastrointestinal digestion device, the reactor lined with a bionic gastrointestinal tract is used to achieve the thermal insulation of samples; the circulating water sandwiched between the reactor and the bionic gastrointestinal tract squeezes the bionic gastrointestinal tract to achieve the reciprocating motion of the samples, thus simulating the digestion of food in the case of real gastric peristalsis.

The present invention uses a way of using a gastric system to simulate three parts of the human stomach: the gastric body, gastric antrum and pylorus, and the latex bionic stomach in three reaction bottles can be independently controlled to be squeezed or not squeezed; such a way has higher similarity in the aspects of structure and functions compared with the real human stomach.

A reaction solution is filtered through a fiber filter membrane to simulate the absorption of the small intestine so that small molecules of nutrients do not enter the large intestine system, thereby providing a more real intestinal environment for the cultivation of intestinal microorganisms in the large intestine system.

The system is modularized, namely, each part is relatively independent, a certain part in the system can be independently reacted and analyzed, and the operation form is more flexible; the number of reactors can be conveniently increased or decreased as needed to make the structure and functions of the digestive system very convenient.

The system is fully automated, namely, the addition of samples, the digestive juice and a buffer, and the peristalsis and emptying of each part of the system are controlled by the PLC according to a predetermined program, so that the operation is more convenient.

The visual bionic gastric body digestion reactor provided by the present invention uses the three reaction bottles to respectively simulate three parts of the human stomach: the gastric body, gastric antrum and pylorus, and the latex bionic stomach in the bottles is squeezed by pressure of the circulating water, thereby simulating the digestion of food in the case of real gastric peristalsis; the reactor has higher similarity compared with the existing simulated gastrointestinal digestion device; the gear pump is used to increase the pressure of circulating water, thereby solving the problem that the circulating water supply pressure of the thermostatic circulating water tank is insufficient to squeeze the latex bionic stomach; the sampling bottle is provided with a screw mouth for capping; the ground opening with the rubber plug is arranged, and sampling can be performed by a syringe; the real-time observation of the change process of the samples in the model is realized, the process data is obtained, and the collection of the process data provides a reference for optimizing the operation parameters of the model; each part is relatively independent and is convenient for disassembly.

The visual in vitro bionic intestinal digestion reactor provided by the present invention, compared with the existing simulated intestinal digestion device, uses the glass reactor in which the latex bionic intestinal tract is sheathed to achieve the thermal insulation of the samples; the pressure of circulating water between the glass bottle and the latex bionic intestinal tract squeezes the latex bionic intestinal tract to achieve the reciprocating motion of the samples, thus simulating the digestion of food in the case of real intestinal peristalsis; the gear pump is used to increase the pressure of circulating water, thereby solving the problem that the circulating water supply pressure of the thermostatic circulating water tank is insufficient to squeeze the latex bionic intestinal tract; the sampling bottle is provided with a screw mouth for capping, and a pH electrode can be inserted; the ground opening with the rubber plug is arranged, and sampling can be performed by a syringe; the real-time observation of the change process of the samples in the model is realized, the process data is obtained, and the collection of the process data provides a reference for optimizing the operation parameters of the model; each part is relatively independent and is convenient for disassembly.

DETAILED DESCRIPTION

Hereinafter, the visual bionic digestive system for a human gastrointestinal tract model provided by the present invention will be further described in detail with reference to the accompanying drawings and specific embodiments. The advantages and characteristics of the present invention will be more apparent from the following description and claims. It should be noted that the accompanying drawings all adopt a very simplified form and all use non-precise proportions, and are only used for convenience and clarity to help illustrate the objectives of the embodiments of the present invention.

Reducing sugars are measured using a DNS method.

Starch refers to an acid hydrolysis method as a second method in GB/T5009.9-2008 "Determination of Starch in Foods".

The protein content is determined using a micro Kjeldahl method.

Example 1

Figure 1:
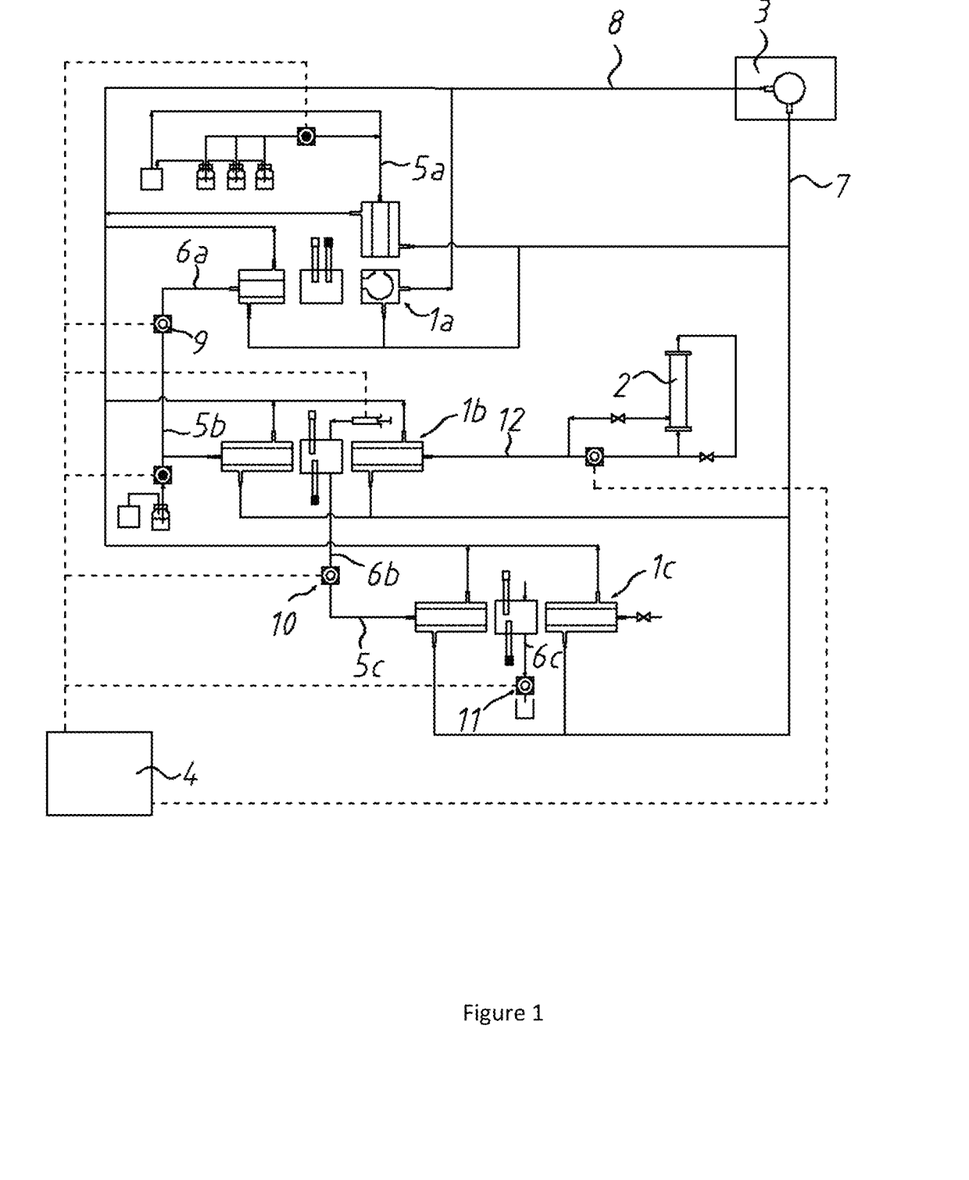
FIG. 1 is a schematic structural diagram of a visual bionic digestive system for a human gastrointestinal tract model.

A visual bionic digestive system for a human gastrointestinal tract model provided by the present Example is shown in FIG. 1, and comprises a reaction system, a control system, and a delivery device. The reaction system comprises a bionic stomach system 1a, a bionic small intestine system 1b, and a bionic large intestine system 1c. The control system comprises a PLC 4, peristaltic pumps 14, and a circulating water tank 3. The delivery device comprises a first gas bottle 25 and a plurality of sample bottles 26.

Example 2

Figure 2:
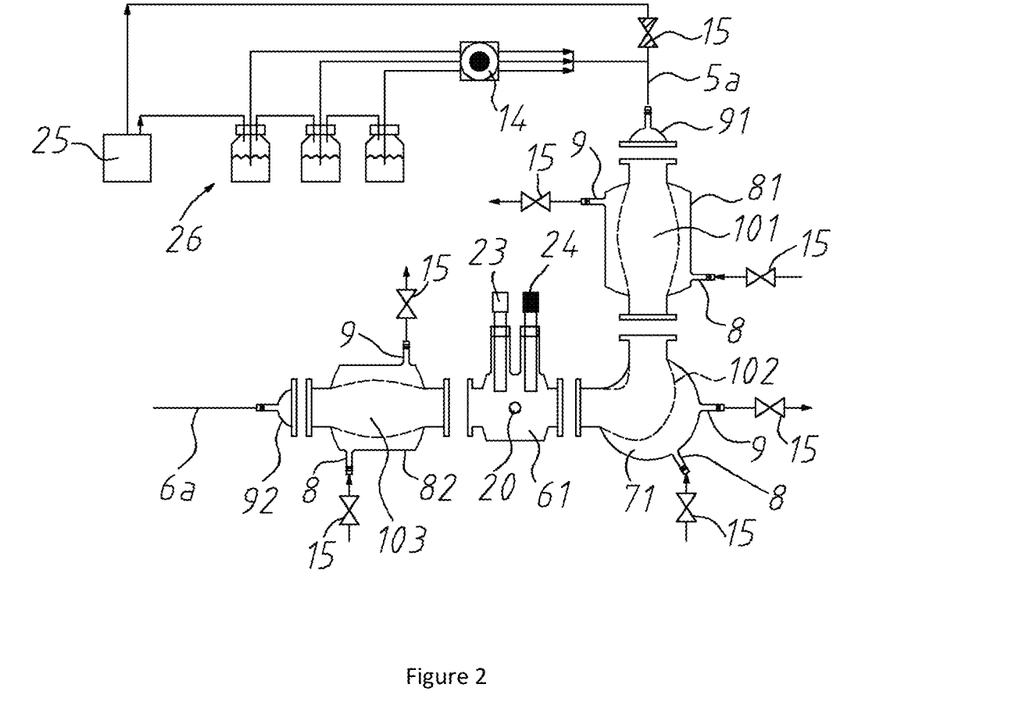
FIG. 2 is a schematic structural diagram of a bionic stomach system.

The bionic stomach system 1a provided by the present Example is shown in FIG. 2. The bionic stomach system 1a is formed by sequentially connecting a first adapter 91, a first cylindrical reactor 81, a spherical reactor 71, a first sampler 61, a second cylindrical reactor 82 and a second adapter 92 through flanges. The first adapter 91 is connected to an input pipe 5a, and the plurality of sample bottles 26 is connected to the input pipe 5a through the peristaltic pump 14. One opening of the first gas bottle 25 is communicated with one of the plurality of sample bottles 26, and the other opening is connected to the input pipe 5a through a solenoid valve 15. The second adapter 92 is connected to an outlet pipe 6a. The bionic stomach system also comprises a latex bionic stomach.

The latex bionic stomach includes a latex bionic gastric body 101, a latex bionic gastric antrum 102, and a latex bionic pylorus 103. The latex bionic gastric body 101 is placed in the first cylindrical reactor 81, both ends of the latex bionic gastric body 101 are respectively extended from the two openings of the first cylindrical reactor 81 to be turned inside out, and the end parts of latex tubes turned inside out to be exposed to the outside of the flanges are sleeved on the flanges. The flange at the opening of the first adapter 91 is butt jointed with the flange at the upper end opening of the first cylindrical reactor 81, and then the two flanges are clamped with a clamp; the latex bionic gastric antrum 102 is placed in the spherical reactor 71, both ends of the latex bionic gastric antrum 102 are respectively communicated with a section of latex tube, the ports of the two sections of latex tubes are respectively extended from the two openings of the spherical reactor 71 to be turned inside out, and the end parts of the latex tubes turned inside out to be exposed to the outside of the flanges are sleeved on the flanges, the flange at the upper end opening of the spherical reactor 71 is butt jointed with the flange at the lower end opening of the first cylindrical reactor 81, and then the two flanges are clamped with a clamp; the flange at the left end opening of the spherical reactor 71 is butt jointed with the flange at the right end of the first sampler 61, and then the two flanges are clamped with a clamp; the latex bionic pylorus 103 is placed in the second cylindrical reactor 82, both ends of the latex bionic pylorus 103 are respectively extended from the two openings of the second cylindrical reactor 82 to be turned inside out, and the end parts of the latex tubes turned inside out to be exposed to the outside of the flanges are sleeved on the flanges, the flange at the right end of the second cylindrical reactor 81 is butt jointed with the flange at the left end of the first sampler 61, and then the two flanges are clamped with a clamp; the flange at the left end of the second cylindrical reactor 82 is butt jointed with the flange at the opening of the second adapter 92, and then the two flanges are clamped with a clamp.

Both the first adapter 91 and the second adapter 92 are hollow hemispheres, flanges are arranged at the openings of the hollow hemispheres, the spherical reactor 71 is a hollow sphere, two mutually vertical openings are formed in the hollow sphere, the two openings divide the great circle of the hollow sphere into a major arc and a minor arc, and an input pipe and an output pipe of a spherical reaction bottle are arranged on the major arc. The first sampler 61 is a hollow tube body, the left end and right end openings of the hollow tube body are respectively provided with a flange, and the side body of the hollow tube body is provided with three glass tubes which are vertically communicated with the hollow tube body; two of the three glass tubes are vertically arranged and provided with upward openings, and the ports of the two glass tubes are provided with external threads; another glass tube is horizontally arranged, the port of the glass tube is provided with a ground opening, and the ground opening is plugged with a rubber plug.

Example 3

Figure 3:
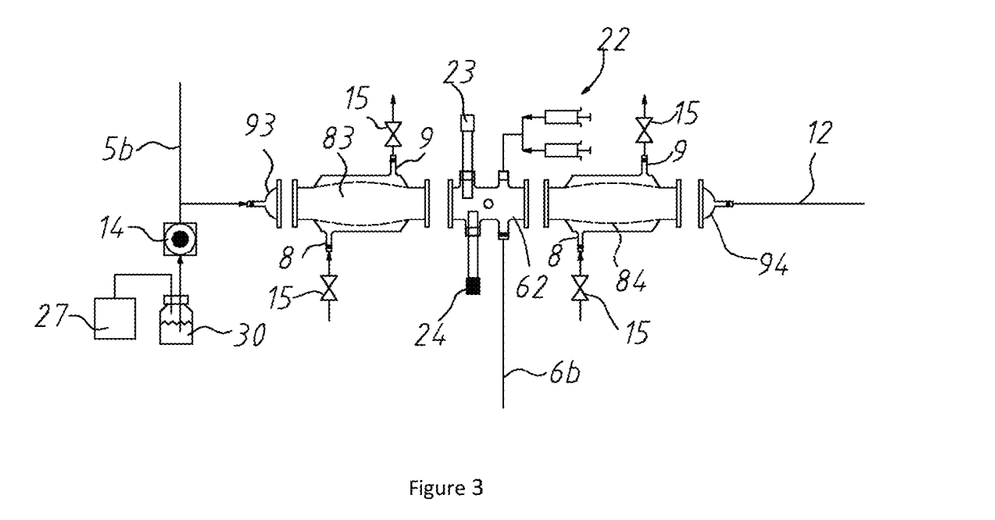
FIG. 3 is a schematic structural diagram of a bionic small intestine system.

The bionic small intestine system 1b provided by the present Example is shown in FIG. 3. The bionic small intestine system 1b is formed by sequentially connecting a third adapter 93, a third cylindrical reactor 83, a second sampler 62, and a fourth cylindrical reactor 84, and a fourth adapter 94 through flanges; the second sampling bottle 62 is provided with a lower end opening and a syringe pump 22, the third adapter 93 is connected to a digestive juice bottle 30 through the peristaltic pump 14, and the digestive bottle 30 is communicated with a second gas bottle 27.

Both the third adapter 93 and the fourth adapter 94 are hollow hemispheres, flanges are arranged at the openings of the hollow hemispheres, the arc top of the third adapter 93 is provided with a sample input pipe 5b, and the arc top of the fourth adapter 94 is provided with a sample output pipe 12. The sample input pipe 5b and the sample output pipe 12 are respectively communicated with silicone tubes, and valves are arranged on the silicone tubes, and used for allowing the samples to be injected into or flow out of a visual in vitro bionic intestinal digestion reactor. Both the third cylindrical reactor 83 and the fourth cylindrical reactor 84 are hollow tube bodies, bionic intestinal tracts are respectively placed in the third cylindrical reactor 83 and the fourth cylindrical reactor 84, both ends of the bionic intestinal tract are respectively extended from the two openings of the hollow tube body to be turned inside out, and the ends of latex tubes turned inside out to be exposed to the outside of flanges are sleeved on the flanges.

Specifically, the second sampler 62 is a hollow tube body as shown in FIG. 3. The left and right end openings of the second sampler 62 are respectively provided with a flange, and the side of the second sampler 62 is provided with five glass tubes which are vertically communicated with the hollow tube body; two of the five glass tubes are provided with vertically upward openings, and the ports of the two glass tubes are provided with external threads; two glass tubes are provided with vertically downward openings, the port of one glass tube is provided with external threads, and the outer wall of the port of the other glass tube is provided with left-handed threads; in addition, one glass tube is horizontally arranged, the port of the glass tube is provided with a ground opening, and the ground opening is plugged with a rubber plug.

Example 4

Figure 4:
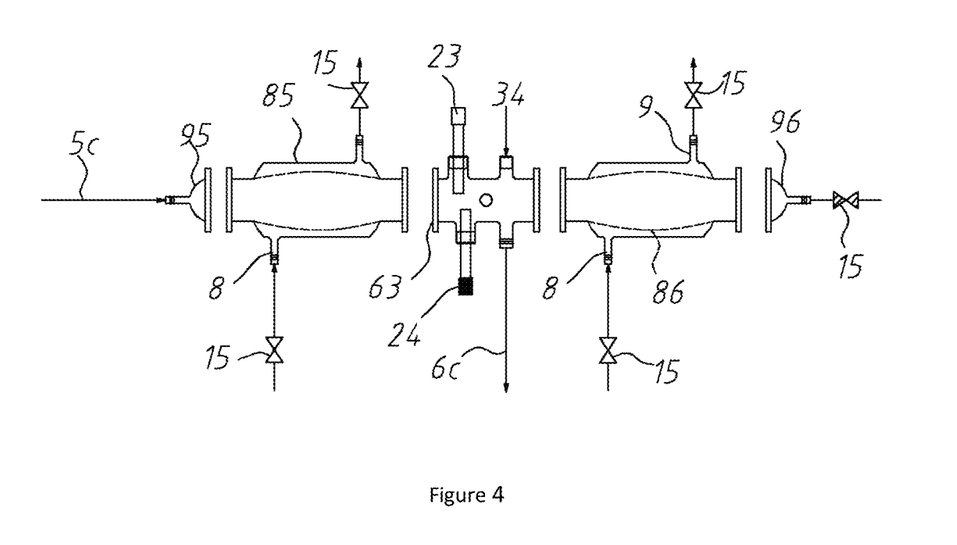
FIG. 4 is a schematic structural diagram of a bionic large intestine system.

As shown in FIG. 4, the bionic large intestine system 1c is formed by sequentially connecting a fifth adapter 95, a fifth cylindrical reactor 85, a third sampler 63, a sixth cylindrical reactor 86, and a sixth adapter 96 through flanges. The fifth adapter 95 is connected to the lower end opening of the second sampling bottle 62 through the peristaltic pump 14, and the third sampling bottle 63 is provided with a lower end opening.

Both the fifth adapter 95 and the sixth adapter 96 are hollow hemispheres, flanges are arranged at the openings of the hollow hemispheres, and the arc top of the fifth adapter 95 is provided with a sample input pipe 5c. Both the fifth cylindrical reactor 85 and the sixth cylindrical reactor 86 are hollow tube bodies, bionic intestinal tracts are respectively placed in the fifth cylindrical reactor 85 and the sixth cylindrical reactor 86, both ends of the bionic intestinal tract are respectively extended from the two openings of the hollow tube body to be turned inside out, and the ends of latex tubes turned inside out to be exposed to the outside of flanges are sleeved on the flanges.

Specifically, the third sampler 63 is a hollow tube body as shown in FIG. 4. The left and right end openings of the third sampler 63 are respectively provided with a flange, and the side of the third sampler 63 is provided with five glass tubes which are vertically communicated with the hollow tube body; two of the five glass tubes are provided with vertically upward openings, and the ports of the two glass tubes are provided with external threads; two glass tubes are provided with vertically downward openings, the port of one glass tube is provided with external threads, and the outer wall of the port of the other glass tube is provided with left-handed threads; in addition, one glass tube is horizontally arranged, the port of the glass tube is provided with a ground opening, and the ground opening is plugged with a rubber plug.

Example 5

Referring to FIG. 1 to FIG. 4, the third adapter 93 of the bionic small intestine system 1b is connected to the input pipe 5b, the lower end opening of the second sampler 62 is connected to an output pipe 6b, and the fourth adapter 94 is connected to the pipe 12; the output pipe 6a and the input pipe 5b are the same pipe, and a peristaltic pump 14 is arranged in the middle of the pipe; the opening of a filtering system is connected to the pipe 12, and the filtering system comprises a fiber filter membrane 21, a peristaltic pump 14, and a solenoid valve 15. The fifth adaptor 95 of the large intestine system 1c is connected to the input pipe 5c, and the lower end opening of the third sampler 63 is connected to the output pipe 6c; the output pipe 6b and the input pipe 5c are the same pipe, and a peristaltic pump 14 is arranged in the middle of the pipe; a peristaltic pump 14 is arranged on the output pipe 6c, and the other end of the output pipe 6c is provided with a collection bottle 28; each reactor is provided with a circulating water inlet and a circulating water outlet, solenoid valves 15 are arranged on all silicon tubes connected to the circulating water inlet and the circulating water outlet, all the circulating water flows from a circulating water outlet pipe 8, and one end of the circulating water outlet pipe 8 is connected to a water outlet of the circulating water tank 3; all the circulating water flows back to a circulating water return pipe 7, and one end of the circulating water return pipe 7 is connected to a water return port of the circulating water tank 3; all the peristaltic pumps 14, syringe pumps 22, and solenoid valves 15 in the visual bionic digestive system for the human intestinal tract model are controlled by the PLC 4.

Specifically, the gas in the first gas bottle 25 and the second gas bottle 27 comprises a mixed gas of $N_2$ and $CO_2$. The first cylindrical reactor 81, the spherical reactor 71, the second cylindrical reactor 82, the third cylindrical reactor 83, the fourth cylindrical reactor 84, the fifth cylindrical reactor 85, and the sixth cylindrical reactor 86 are all provided with the circulating water inlet 8 and the circulating water outlet 9, and solenoid valves 15 are arranged on silicon tubes connected to the circulating water inlet 8 and the circulating water outlet 9. The first sampling bottle 61, the second sampling bottle 62, and the third sampling bottle 63 are provided with a pH electrode probe 23 and a microscope probe 24, wherein the second sampling bottle 62 is also provided with a lower end opening and a syringe pump, and the third sampling bottle 63 is also provided with an inoculation port 34 and a lower end opening. The lower end opening of the second sampling bottle 62 is connected to the outlet pipe 6b, and the lower end opening of the third sampling bottle 63 is connected to the outlet pipe 6c.

Example 6

Simulation experiments of the visual bionic digestive system for a human gastrointestinal tract model are as follows.

In the present Example, the visual bionic digestive system for a human gastrointestinal tract model is used to evaluate the simulated effect of the visual bionic digestive system for a human gastrointestinal tract model through an experiment of digesting food samples in reactors.

Referring to FIG. 2, before the reaction was started, the solenoid valve 15 was opened, and the mixed gas of $N_2$ and $CO_2$ is introduced into the system so that the residual gas in the system was exhausted to create an oxygen-free environment; then the solenoid valve 15 was closed to start the peristaltic pump 14, and a certain amount of sample, gastric juice and HCl were added into the bionic stomach system 1a from the inlet pipe 5a; in the stomach system, the sample was repeatedly squeezed among the first cylindrical reactor 81, the spherical reactor 71, and the second cylindrical reactor 82, and the sample was ground and decomposed into micromolecular substances; after reacting for a period of time, the sample was discharged through the outlet pipe 6a.

Referring to FIG. 3, the sample discharged from the bionic stomach system 1a enters the bionic small intestine system 1b through the input pipe 5b; a certain amount of $Na_2HCO_3$ was added into the bionic small intestine system 1b, the syringe pump 22 was started, a certain amount of pancreatic juice and bile were added into the bionic small intestine system 1b, the sample was repeatedly squeezed between the third cylindrical reactor 83 and the fourth cylindrical reactor 84, and the sample was further ground and decomposed; after reacting for a certain period of time, the sample entered the filtering system through the pipe 12; after the sample was filtered by the filtering system, micromolecular substances such as monosaccharides and amino acids in the sample were removed as a filtrate, and the remaining macromolecular substances and part of water flowed back to the small intestine system through the pipe 12, and then were discharged through the output pipe 6b.

Referring to FIG. 4, the sample discharged from the bionic small intestine system 1b entered the bionic large intestine system 1c through the inlet pipe 5c; the bionic large intestine system 1c was inoculated with intestinal microorganisms through an inoculation port 34 of the third sampling bottle 63; in the bionic large intestine system 1c, the sample and the intestinal microorganisms were repeatedly squeezed between the fifth cylindrical reactor 85 and the sixth cylindrical reactor 86, and the sample was decomposed and fermented by the microorganisms. After reacting for a period of time, the sample was discharged into the collection bottle 28 through the outlet pipe 6c.

The sample was taken from a sampling port in the corresponding sampling bottle in the respective bionic system in the reaction processes of the bionic stomach system 1a, the bionic small intestine system 1b, and the bionic large intestine system 1c, and the percentage of the ground and digested part of the sample in the sample was detected; the pH value of each measuring point was obtained by the pH electrode; the change in the sample at each measuring point and the growth condition of the intestinal microorganisms were obtained from the microscope.

Example 7

The digestion of the human gastrointestinal tract is a complex process. The traditional simulated gastrointestinal digestion reactor belongs to a static simulated digestion. It cannot simulate the physical and physiological processes of foods in the gastrointestinal tract, such as a change in pH, the peristalsis of gastrointestinal walls, the emptying of chyme in stomach. After a thermostatic water bath shaker, a magnetic stirrer, an up-down moving mixer and other instruments were generally used to simply mix the food and the simulated gastrointestinal juice once, the mixed food and simulated gastrointestinal juice were placed in a 37° C. water bath and stirred for 1 to 2 h to simulate the gastrointestinal digestive process of the food.

The present invention is a dynamic digestion model which is closer to the real gastrointestinal tract and can well enable the fluid dynamics, peristaltic contraction and the like in the gastrointestinal tract to reoccur and comprehensively simulate the physical process and physiological process in the gastrointestinal tract.

First Step: Preparation of Food Suspension

An appropriate amount of food powder was weighed and diluted into a suspension with a 0.2% (w/v) guar gum solution.

Food powder formula: corn flour: 100 g, concentrated whey protein powder: 40 g, and edible salt: 1 g.

Second Step: Addition of Samples

Referring to FIGS. 1 to 4, a certain amount of 0.1 mol/L hydrochloric acid and a certain amount of simulated gastric juice composed of pepsin, KCl, and NaCl were injected into the bionic stomach system 1a to simulate the gastric digestion environment. A certain amount of 0.1 mol/L $NaHCO_3$ and a certain amount of pancreatic juice and intestinal juice were injected into the bionic small intestine system 1b to simulate the intestinal digestive environment.

Third Step: Working Process

Before adding food samples, 0.6 mL of simulated gastric juice was injected to simulate a gastric juice residue in the fasted state. In order to more really simulate the process of ingesting corn flour and the oral digestive process, the food samples were added from the simulated esophagus into the stomach model in a batched manner, and the injection time lasted for 5 min. During the injection, the input rate of the simulated gastric juice was precisely controlled by the syringe pump. At the end of the injection, the simulated gastric antrum and pylorus were closed to simulate the digestive process of food without gastric emptying. At the same time, the pylorus and gastric antrum of the stomach model were compressed by water pressure, and the compression frequency was 3 times per minute and the compression amplitude was 2.5 mm. After the food samples were digested for 1 h, the intragastric digestion products entered the bionic small intestine system 1b in a peristaltic manner, the food samples were added from the simulated esophagus to the bionic small intestine system 1b model in a batch manner, and the injection time lasted for 10 min. During the injection, the input rates of the simulated intestinal juice and pancreatic juice were precisely controlled by the syringe pump. After the injection was completed, the intestinal tract was peristaltically compressed by water pressure, the peristaltic compression frequency was 10 times per minute and the compression amplitude was 1 cm. After the food samples were digested for 3 h, the intestinal digestion products were completely removed and the starch hydrolysis rate and the protein content were measured. The digestive results of the visual bionic intestinal digestion reactor provided by the present invention, the existing bionic reactor and the intestinal tract of a mouse are compared as shown in FIG. 5.

Figure 5:
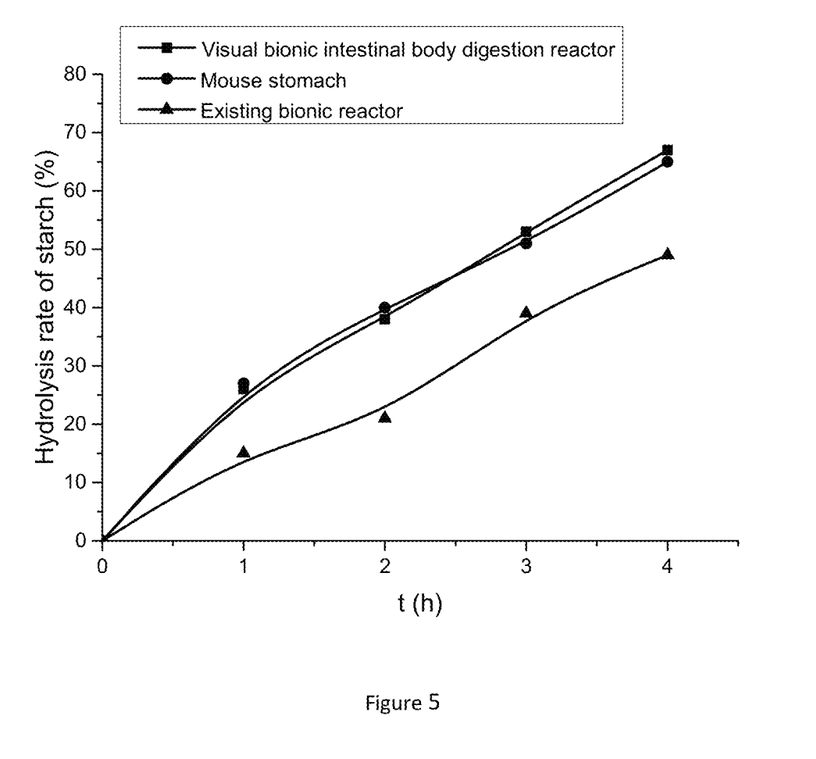
FIG. 5 is a comparison diagram of digestion results of a bionic digestion reactor for the gastrointestinal tract model provided by the present invention, the existing bionic reactor and the mouse intestinal tract.

As can be seen from FIG. 5, compared with the traditional bionic reactor, the bionic reactor provided by the present invention can more realistically simulate the process results of digesting foods in the stomach of living mice, which shows the obvious advantages of the bionic reactor provided by the present invention.

Example 8

The digestion of the human stomach is a complex process. The traditional simulated gastric digestion reactor belongs to a static simulated digestion. It cannot simulate the physical and physiological processes of foods in the body, such as a change in pH, the peristalsis of gastric wall, the emptying of chyme in stomach. After the thermostatic water bath shaker, the magnetic stirrer, the up-down moving mixer and other instruments were generally used to simply mix the food and the simulated gastric juice once, the mixed food and simulated gastric juice were placed in a 37° C. water bath and stirred for 1 to 2 h to simulate the gastric digestive process of the food.

The bionic gastric system 1a shown in FIG. 2 provided by the present invention is a dynamic digestion model which is closer to the real gastric tract and can well enable the fluid dynamics, peristaltic contraction, the emptying of chyme and the like in the gastric tract to reoccur and comprehensively simulate the physical process and physiological process in the gastric tract.

First Step: Preparation of Food Suspension

An appropriate amount of food powder was weighed and diluted into a suspension with a 0.2% (w/v) guar gum solution.

Food powder formula: corn flour: 100 g, concentrated whey protein powder: 40 g, and edible salt: 1 g.

Second Step: Addition of Samples

Referring to FIG. 2, the food suspension was injected into the visual in vitro bionic human stomach digestion reactor through the input pipe 5a of the first adapter 91 at a certain flow rate, and then a certain amount of 0.1 mol/L hydrochloric acid and a certain amount of simulated gastric juice composed of pepsin, KCl, and NaCl were injected into the visual in vitro bionic human stomach digestion reactor through the input pipe 5a.

Third Step: Working Process (1) The input pipe 5a and the output pipe 6a were closed, the output pipe 9 and the input pipe 8 on the first cylindrical reactor 81, the output pipe 9 and the input pipe 8 on the spherical reactor 71, and the output pipe 9 and the input pipe 8 on the second cylindrical reactor 82 were opened, and the gear pump on the total input silicone tube connected to the water outlet of the thermostatic circulating water tank was turned on so that an interlayer between the reaction bottle and the latex bionic stomach was full of circulating water; (2) the outlet pipe 9 and the inlet pipe 8 on the first cylindrical reactor 81, the outlet pipe 9 on the spherical reactor 71, and the outlet pipe 9 on the second cylindrical reactor 82 were closed so that the circulating water continuously flowed into an interlayer between the spherical reactor 71 and the second cylindrical reactor 82, under the pressure of circulating water, the latex bionic gastric antrum 102 and the latex bionic pylorus 103 were squeezed and the internal sample thereof was squeezed into the latex bionic gastric body 101; (3) the input pipe 8 on the first cylindrical reactor 81 was opened, and the outlet pipe 9 on the first cylindrical reactor 81, the output pipe 9 on the second cylindrical reactor 82, the input pipe 8 on the spherical reactor, and the input pipe 8 and the output pipe 9 on the second cylindrical reactor 82 were closed so that the circulating water continually flowed into the interlayer of the second cylindrical reactor 82, under the pressure of circulating water, the latex bionic gastric body 101 was squeezed, and the internal sample thereof was squeezed into the latex bionic gastric antrum 102 and the latex bionic pylorus 103; (4) the input pipe 8 on the first cylindrical reactor 81 and the input pipe 8 on the spherical reactor 71 were opened, and the output pipe 9 on the first cylindrical reactor 81, the output pipe 9 on the spherical reactor 71, and the output pipe 9 and the input pipe 8 on the second cylindrical reactor 82 were closed so that the circulating water continuously flowed into the interlayer between the first cylindrical reactor 81 and the spherical reactor 71, under the pressure of circulating water, the latex bionic gastric body 101 and the latex bionic pylorus 103 were squeezed, and the internal samples thereof were squeezed into the latex bionic gastric antrum 102 in the second cylindrical reactor 82. Steps (2) to (4) were repeatedly operated.

Before adding food samples, 0.6 mL of simulated gastric juice was injected to simulate a gastric juice residue in the fasted state. In order to more really simulate the process of ingesting corn flour and the oral digestive process, the food samples were added from the simulated esophagus into the stomach model in a batched manner, and the injection time lasted for 5 min. During the injection, the input rate of the simulated gastric juice was precisely controlled by the syringe pump. At the end of the injection, the simulated gastric antrum and pylorus were closed to simulate the digestive process of food without gastric emptying. At the same time, the pylorus and gastric antrum of the stomach model were compressed by water pressure, and the compression frequency was 3 times per minute and the compression amplitude was 2.5 mm. After the food samples were digested for 60 min, the intragastric digestion products were completely removed and the reducing sugar and protein contents were measured. The digestive results of the visual bionic gastric body digestion reactor provided by the present invention, the existing bionic reactor and the stomach of a mouse are compared as shown in FIG. 6.

Figure 6:
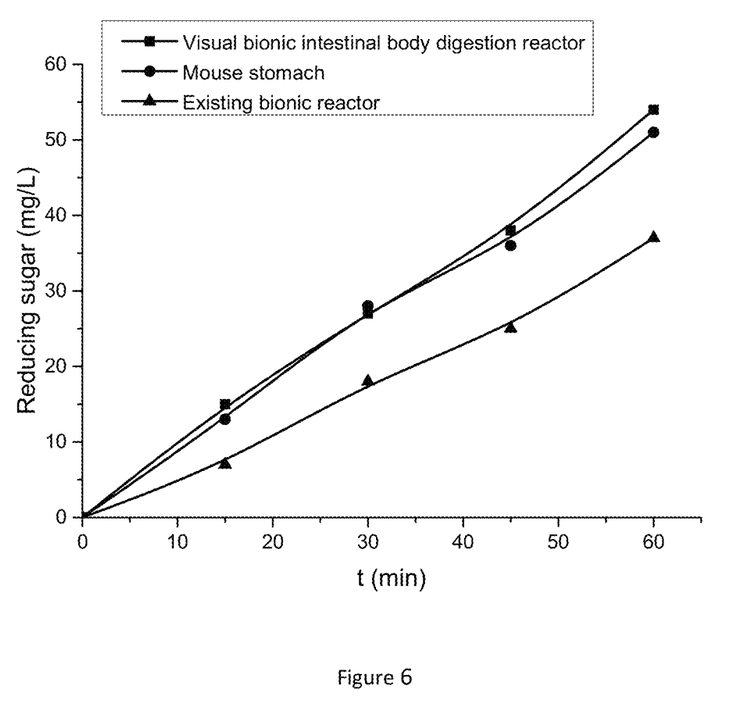
FIG. 6 is a comparison diagram of digestion results of a visual bionic gastric body digestion reactor, the existing bionic reactor, and the mouse stomach.

As can be seen from FIG. 6, compared with the traditional bionic reactor, the bionic reactor provided by the present invention can more realistically simulate the process results of digesting foods in the stomach of living mice, which shows the obvious advantages of the bionic reactor provided by the present invention.

Example 9

The digestion of the human intestinal tract is a complex process. The traditional intestinal simulated digestion reactor belongs to a static simulated digestion. It cannot simulate the physical and physiological processes of foods in the intestinal tract, such as a change in pH and the peristalsis of intestinal wall. In the prior art, after the thermostatic water bath shaker, the magnetic stirrer, the up-down moving mixer and other instruments were generally used to simply mix the food and the simulated intestinal juice once, the mixed food and simulated intestinal juice were placed in a 37° C. water bath and stirred for 1 to 2 h to simulate the intestinal digestive process of the food.

The bionic small intestinal system 1b provided by the present invention is a dynamic digestion model which is closer to the real intestinal tract and can well enable the fluid dynamics, peristaltic contraction and the like in the intestinal tract to reoccur and comprehensively simulate the physical process and physiological process in the intestinal tract.

First Step: Preparation of Food Suspension

An appropriate amount of food powder was weighed and diluted into a suspension with a 0.2% (w/v) guar gum solution.

Food powder formula: corn flour: 100 g, concentrated whey protein powder: 40 g, and edible salt: 1 g.

Second Step: Addition of Samples

Referring to FIG. 3, the food sample was injected into the visual in vitro bionic intestinal digestion reactor through the input pipe 5b of the third adapter 93 at a certain flow rate, and then a certain amount of 0.1 mol/L $NaHCO_3$ and a certain amount of pancreatic juice and intestinal juice were injected into the visual in vitro bionic human intestinal digestion reactor through the input pipe 5b.

Third Step: Working Process (1) The input pipe 5b and the output pipe 12 were closed, the valves on the silicone tubes connected to the output pipe 9 and the input pipe 8 on the third cylindrical reactor 83 and the fourth cylindrical reactor 84 were opened, and the gear pump on the total input silicone pipe connected to the water outlet of the thermostatic circulating water tank was turned on so that an interlayer between the two reaction bottles and the latex bionic intestinal tract was full of circulating water; (2) the valve on the silicone tube connected to the input pipe 8 on the third cylindrical reactor 83 was opened, and the valves on the silicone tubes, connected to the output pipes 9 on the third cylindrical reactor 83 and the fourth cylindrical reactor 84 and the input pipe 8 on the fourth cylindrical reactor 84 were closed, so that the circulating water continuously flowed into an interlayer in the third cylindrical reactor 83, under the pressure of circulating water, the bionic intestinal tract in the third cylindrical reactor 83 was squeezed and the internal sample was squeezed into the bionic intestinal tract in the fourth cylindrical reactor 84; (3) the valve on the silicone tube connected to the input pipe 8 on the fourth cylindrical reactor 84 was opened, and the valves on the silicone tubes, connected to the input pipe 8 and the output pipe 9 on the third cylindrical reactor 83 and the output pipe 9 on the fourth cylindrical reactor 84 were closed, so that the circulating water continually flowed into the interlayer of the fourth cylindrical reactor 84, under the pressure of circulating water, the bionic intestinal tract in the fourth cylindrical reactor 84 was squeezed, and the internal sample thereof was squeezed into the bionic intestinal tract in the third cylindrical reactor 83; steps (2) to (3) were repeatedly operated.

Before adding food samples, 0.6 mL of simulated intestinal juice and pancreatic juice were injected to simulate the digestive environment in the intestinal tract. In order to more really simulate the process of ingesting corn flour, the food samples were added from the simulated esophagus into the gastrointestinal tract model in a batched manner, and the injection time lasted for 10 min. During the injection, the input rates of the simulated intestinal juice and pancreatic juice were precisely controlled by the syringe pump. At the end of the injection, the intestinal tract was peristaltically compressed by water pressure, and the peristaltic compression frequency was 10 times per minute and the compression amplitude was 1 cm. After the food samples were digested for 3 h, the intestinal digestion products were completely removed and the reducing sugar and protein contents were measured. The digestive results of the visual bionic intestinal digestion reactor provided by the present invention, the existing bionic reactor and the intestinal tract of a mouse are compared as shown in FIG. 7.

Figure 7:
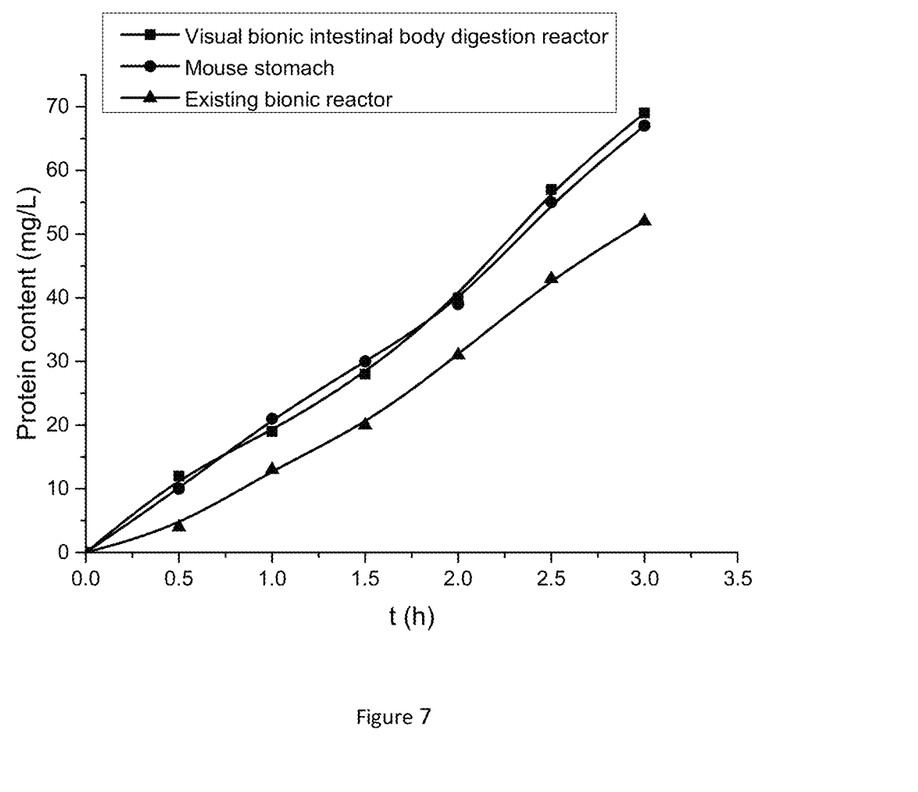
FIG. 7 is a comparison diagram of digestion results of a visual bionic intestinal body digestion reactor, the existing bionic reactor, and the mouse stomach.

As can be seen from FIG. 7, compared with the traditional bionic reactor, the bionic reactor provided by the present invention can more realistically simulate the process results of digesting foods in the stomach of living mice, which shows the obvious advantages of the bionic reactor provided by the present invention.

Control Example 1

A set of control experiments was designed to explore the influence whether the circulating water is introduced or not on the simulated digestion effect of the visual bionic gastric body digestion reactor.

Referring to FIG. 2, the visual bionic gastric body digestion reactor was used for the control experiment. In the control experiment, all the circulating water inlet pipes 8 were closed so that the circulating water could not flow into the reaction bottles; before adding the food samples, 0.6 mL of simulated gastric juice was injected to simulate the gastric juice residue in the fasted state. In order to more really simulate the process of ingesting corn flour and the oral digestive process, the food samples were added from the simulated esophagus into the stomach model in a batched manner, and the injection time lasted for 5 min. During the injection, the input rate of the simulated gastric juice was precisely controlled by the syringe pump. At the end of the injection, the simulated gastric antrum and pylorus were closed to simulate the digestive process of food without gastric emptying. At the same time, the pylorus and gastric antrum of the stomach model were compressed by water pressure, and the compression frequency was 3 times per minute and the compression amplitude was 2.5 mm. After the food samples were digested for 60 min, the intragastric digestion products were completely removed and the reducing sugar and protein contents were measured.

When the circulating water did not flow into the glass reaction bottles, the sample could only stay in the latex bionic stomach of a reaction bottle. For example, if the sample and the digestive juice flowed into the visual bionic gastric body digestion reactor through the input pipe 5a, the sample and the digestive juice were almost entirely deposited in the latex bionic gastric antrum 102 of the spherical reaction bottle. At this time, the sample and the digestive juice could flow into the latex bionic pylorus 103 only by means of the external peristaltic pump, and then flow out of the output pipe 6a. In such a way, the sample and the digestive juice could not be fully mixed and the particulate matter contained in the sample could not be ground and dissolved due to the absence of pressure, so the simulated digestion effect was poor.

When the circulating water flowed into the reaction bottles, the sample and the digestive juice could reciprocally flow in the latex bionic organs of the three reaction bottles. For example, if the sample and the digestive juice flowed into the visual bionic gastric body digestion reactor through the input pipe 5a, the sample and the digestive juice flowed into the latex bionic gastric antrum 102. At this time, the circulating water inlet pipes 8 of the spherical reactor 71 and the second cylindrical reactor 82 were opened, so that the latex bionic gastric antrum 102 and the latex bionic pylorus 103 were squeezed by the circulating water, and the sample and the digestive juice flowed into the latex bionic gastric body 101; the circulating water input pipe 8 on the first cylindrical reactor 81 was opened again, and the circulating water input pipe 8 on the second cylindrical reactor 82 was closed, so that the latex bionic gastric body 101 and the latex bionic gastric antrum 102 were squeezed by the circulating water, and the sample and the digestive juice flowed into the latex bionic pylorus 103. By repeating such operations, the reciprocating motion of the sample and the digestive juice among the three reaction bottles could be achieved to achieve the purpose of mixing the sample and digestive juice, and grinding and dissolving the particulate matter in the sample.

Through the control experiments, it was found that when the circulating water was not introduced into the visual bionic gastric body digestion reactor, the sample flowing through the reactor could not be fully mixed and the particulate matter in the sample could not be dissolved; when the circulating water was introduced into the visual bionic gastric body digestion reactor, and the third step of Example 1 was performed, the same batch of samples flowing through the reactor were thoroughly mixed, and the particulate matter in the samples was dissolved and the samples were in a uniform state.

What is claimed is:

1. A system comprising a reaction system and a control system,
    wherein the reaction system comprises a bionic stomach system, a bionic small intestine system, and a bionic large intestine system;
    wherein the control system comprises a Programmable Logic Controller (PLC), peristaltic pumps, and a circulating water tank;
    wherein the bionic stomach system, the bionic small intestine system, and the bionic large intestine system each comprise water inlet pipes and water outlet pipes;

wherein the water inlet pipes of the bionic stomach system, the bionic small intestine system, and the bionic large intestine system are connected to a water outlet of the circulating water tank;

wherein the water outlet pipes of the bionic stomach system, the bionic small intestine system, and the bionic large intestine system are connected to a water inlet of the circulating water tank;

wherein the PLC is configured to control flow between the circulating water tank and the bionic stomach system, the bionic small intestine system, and the bionic large intestine system;

wherein the bionic stomach system, the bionic small intestine system, the bionic large intestine system or any combination thereof comprises a bionic gastrointestinal tract inside a reactor;

wherein a space between the bionic gastrointestinal tract and the reactor is configured to accommodate water circulating between the circulating water tank and the bionic stomach system; and wherein the PLC is configured to cause a reciprocating motion of a sample inside the bionic gastrointestinal tract by varying a pressure of the water.

2. The system according to claim 1, further comprising a sample delivery device;

wherein the sample delivery device comprises a first gas bottle and a plurality of sample bottles;

wherein the plurality of sample bottles is connected to the bionic stomach system through the peristaltic pumps;

wherein one opening of the first gas bottle is communicated with one of the plurality of sample bottles, and another opening is connected to the bionic stomach system.

3. The system according to claim 1, wherein that the bionic stomach system comprises a first adapter, a first cylindrical reactor, a spherical reactor, a first sampler, a second cylindrical reactor, and a second adapter serially connected by flanges;

wherein the bionic stomach system is configured to receive a sample from the first adapter and configured to output the sample from the second adapter;

wherein the second adapter is connected to the bionic small intestine system through the peristaltic pumps.

4. The system according to claim 1, wherein the bionic small intestine system comprises a third adapter, a third cylindrical reactor, a second sampler, a fourth cylindrical reactor, and a fourth adapter serially connected by flanges;

wherein the second sampler comprises a lower end opening and a syringe pump, the third adapter is connected to a digestive juice bottle through the peristaltic pumps, and the digestive juice bottle is communicated with a second gas bottle.

5. The system according to claim 1, wherein the bionic large intestine system comprises a fifth adapter, a fifth cylindrical reactor, a third sampler, a sixth cylindrical reactor, and a sixth adapter serially connected by flanges;

wherein the fifth adapter is connected to the lower end opening of the second sampler through the peristaltic pumps, and the third sampler comprises a lower end opening.

6. The system according to claim 1, further comprises a filter connected to a fourth adapter of the bionic small intestine system.

7. The system according to claim 1, wherein the first sampler of the bionic stomach system, the second sampler of the bionic small intestine system and the third sampler of the bionic large intestine system each comprise two glass tubes configured to receive pH electrode probes and microscope probes.

8. The system according to claim 4, wherein the PLC is configured to control the peristaltic pumps and the syringe pumps.

9. The system according to claim 2, wherein the first gas bottle is configured to be filled with a mixed gas of $N_2$ and $CO_2$.

10. The system according to claim 7, wherein the third sampler comprises an inoculation port configured for inoculating the large intestine system with intestinal microorganisms.

* * * * *